United States Patent [19]
Jorgens

[11] Patent Number: 5,317,272
[45] Date of Patent: May 31, 1994

[54] PROCESS AND APPARATUS EMPLOYING A STREAM OF ELECTROLYTIC LIQUID FOR EXAMINING THE POROSITY OF COATED OBJECTS

[76] Inventor: Klaus Jorgens, Am Flothen 98, D-5600 Wuppertal 1, Fed. Rep. of Germany

[21] Appl. No.: 929,788

[22] Filed: Aug. 13, 1992

[30] Foreign Application Priority Data

Aug. 22, 1991 [DE] Fed. Rep. of Germany ....... 4127740

[51] Int. Cl.⁵ .................... G01N 27/00; G01N 15/08; C25D 5/00; G01R 31/00
[52] U.S. Cl. .................... 324/558; 118/665; 427/10
[58] Field of Search ............... 324/514, 554, 557, 558, 324/559; 118/665, 712; 427/10; 340/675

[56] References Cited

U.S. PATENT DOCUMENTS

| | | | |
|---|---|---|---|
| 3,343,081 | 9/1967 | Lane | 324/558 |
| 3,792,458 | 2/1974 | Smith et al. | 324/558 X |
| 4,558,273 | 12/1985 | Nishimura | 324/558 |

FOREIGN PATENT DOCUMENTS

| | | | |
|---|---|---|---|
| 0020141 | 2/1985 | Japan | 324/554 |
| 0706762 | 12/1979 | U.S.S.R. | 324/514 |

*Primary Examiner*—Gerard R. Strecker
*Attorney, Agent, or Firm*—Ostrolenk, Faber, Gerb & Soffen

[57] ABSTRACT

Process and apparatus for examining the porosity of coated objects, and in particular of enamelled, electrically conductive strip and profiled material or objects, and in particular of hollow bodies such as beverage cans, in which electrical contact is made with the strip and profiled material or the hollow body to form one pole for an applied test voltage, an electrically conductive connection is made to a coated surface of the strip and profiled material or to the hollow body by means of a continuous stream or curtain of electrolytic fluid emanating from a nozzle, to form the opposite pole for the applied test voltage and wherein the current flowing from the one pole through a stream or curtain of liquid and the coating to the other pole is measured as a measure of the porosity of the coating.

19 Claims, 2 Drawing Sheets

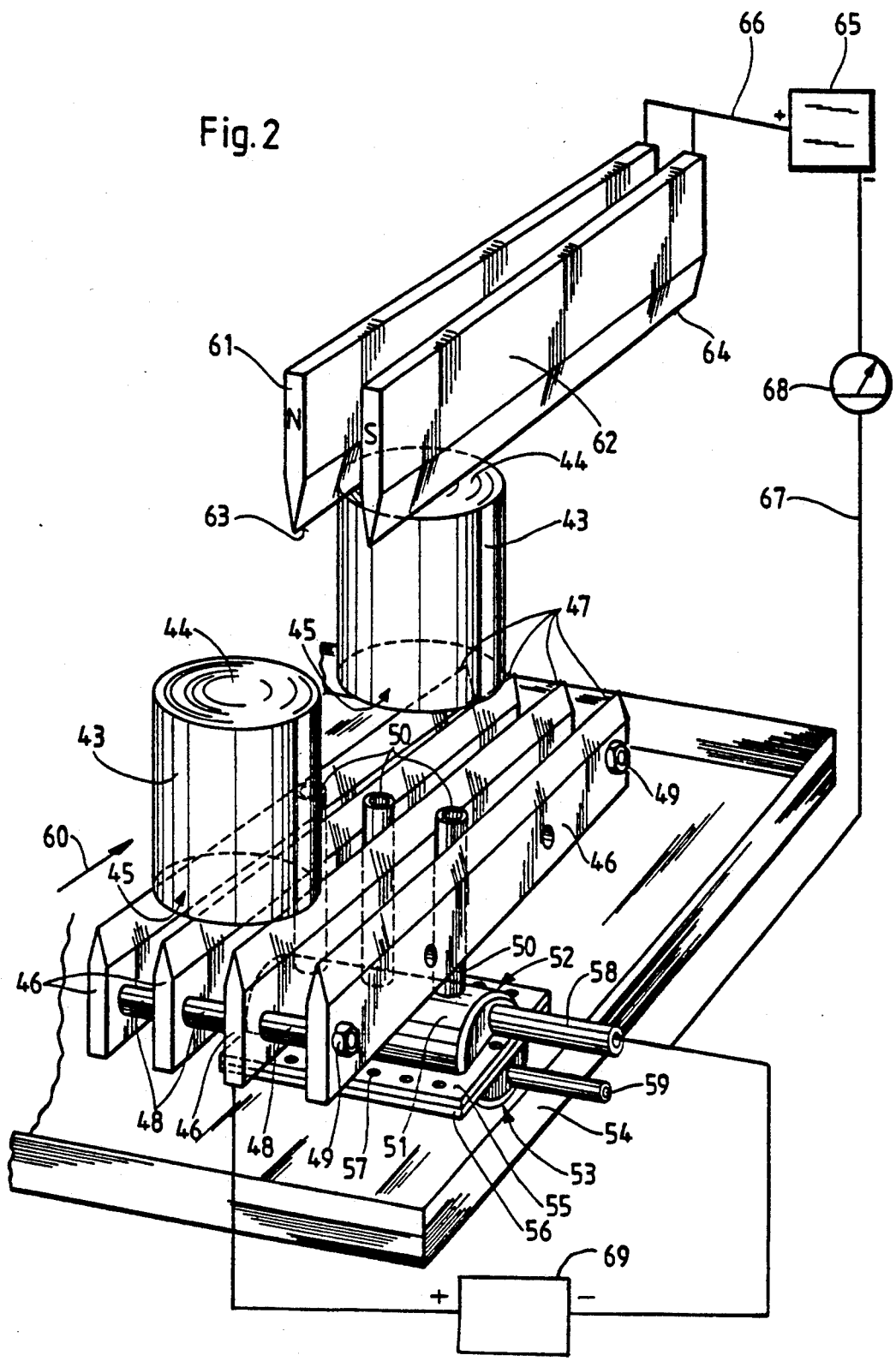

PROCESS AND APPARATUS EMPLOYING A STREAM OF ELECTROLYTIC LIQUID FOR EXAMINING THE POROSITY OF COATED OBJECTS

BACKGROUND OF THE INVENTION

The invention relates to a process and apparatus used to test the porosity of coated objects and, in particular, of enamelled, electrically conductive strip and profiled materials or objects or of hollow bodies such as beverage cans.

The porosity of such coatings when applied to hollow bodies can be measured by filling the hollow body with an electrolytic fluid, applying to the hollow body one pole of a test voltage and applying the other pole to an electrode immersed in the electrolytic liquid and measuring the flow of current. The test voltage will as a rule be 6.3 V. If the coating exhibits no porosity, no current flow will be indicated. Depending on quality requirements, a certain degree of porosity may be tolerated and this can be defined by specifying a permissible maximum value for the flow of current. If the permissible threshold value is exceeded the hollow body will have to be marked and/or rejected and may possibly be recoated.

The method described above for the testing of the porosity of beverage cans is time-consuming and costly since it is necessary to fill the beverage cans individually with electrolytic fluid, make the measurement and then to empty, rinse and dry the beverage cans. For this reason the test process known in the art is performed only on a spot-check basis following the coating of the beverage cans.

The procedure described above can be applied only in testing the porosity of the internal coating of beverage cans and similar hollow bodies, but not in testing coated strip and profiled material.

SUMMARY OF THE INVENTION

The object of the invention is to provide a process and apparatus for testing the porosity of coated objects, such as coated strip and profiled material, as well as other objects and in particular of hollow bodies such as beverage cans, by means of which this test can be performed simply and quickly, so that 100 per cent inspection can be performed instead of spot checks and such that these are suitable for every type of coating and in particular for electrocoated strip or profile material or other enamelled objects.

Based on the foregoing and other objects, the invention contemplates a process of testing the porosity of coated objects in which an electrical contact is made with the object in order to form one pole for an applied test voltage, that a further electrically conductive connection is made to a coated surface of the object, this being by means of a continuous stream of an electrolytic fluid to form the opposite pole for the applied test voltage and that the current flowing from one pole through the stream of liquid and the coating to the other pole is measured and used to test the porosity of the coating.

Based on the foregoing and other objects, the invention further contemplates a process for testing the porosity of electrocoated objects in which an electrical contact is made with the object subsequent to electrocoating but before rinsing and drying to form one pole for an applied test voltage, an electrically conductive connection is made to a coated surface of the object by means of a paint or its permeate derived by means of ultrafiltration serving as the electrolytic liquid, forming the other pole for the applied test voltage, whereby at least one pole of the test circuit is isolated electrically from the anode or cathode of the electrocoating system and whereby the current flowing from one pole through the enamel or the permeate and the coating to the other pole is measured and used as a measure of the porosity of the coating.

The invention is particularly effective in testing the porosity of coated objects, such as coated strips, profiled materials and hollow bodies, such as beverage cans.

The invention is based on the idea of submerging the strip and profiled materials or the objects in an electrolyte bath or of applying to the coated surface of the strip or profile material or the objects a stream or curtain of liquid of electrolytic fluid in such a way that a continuous electrical connection is maintained between the electrolytic fluid which is in contact with one pole of the test voltage and between the other pole which is in contact with the strip or profile or the objects and thus that the measurement voltage is maintained. This continuous stream or curtain of liquid can be directed so that the electrolytic fluid completely covers the surface of the strip and profile material or of the objects to which the liquid is applied in a continuous layer so that the flow of current between the poles of the applied test voltage can serve as a measure of the porosity of the coating.

Trials have surprisingly revealed that both the electrical connection by way of the stream or curtain of liquid made of electrolytic fluid and the immersion in electrolytic fluid are suitable to conduct a measurement of sufficient accuracy.

If the strip or profile material or the objects are not submerged in the bath of electrolyte they can be passed by the stream or curtain of liquid at greater speed and the porosity can nonetheless be measured continuously in the desired fashion and for the entire surface of the strip and profiled material and all objects passed by. The strip or profiled material or the objects can be moved discontinuously or continuously through the area covered by the stream or curtain of liquid.

If the measurement voltage is applied with the object immersed, the porosity test is made subsequent to immersion and in synchronization with the electrocoating cycles.

If all surfaces of the strip or profile material and the outer and inner surfaces of hollow bodies are to be tested for porosity, it is possible to simultaneously or sequentially direct a continuous stream or curtain of liquid at each of these surfaces. The flows of currents to the various surfaces can preferably be measured independently of each other, which is advantageous if the coatings on the various surfaces differ or if there are differing requirements in regard to the porosity.

The innovative process can be conducted in a particularly simple fashion if a water-based enamel or its permeate, derived by means of ultrafiltration, is used as the electrolyte and if this enamel is used to coat the surfaces prior to the porosity test. Water-based enamels are always electrically conductive and thus exhibit consistent electrolytic properties, so that this enamel can be used without difficulty as the electrolyte for testing the porosity. If one wishes to avoid applying additional pigment while testing for porosity, the permeate derived from the water-based enamel by ultrafiltration can be utilized. This permeate is always created whenever undesirable chemical compounds are formed in water-based enamel which dissolve in water and which pass through the ultrafilter during ultrafiltration whereby the pigments and binders required for coating remain in the solution.

The innovative process can be employed to particular advantage when an enamel or its permeate is used as the electrolyte in anodic or cathodic electrocoating.

Since during electrocoating the phenomenon of electrophoresis, i.e. the migration of the charged particles to the anode or to the cathode, is invoked when a direct current voltage is applied whereby the enamel particles neutralized with amines coagulate on the workpiece forming a film, a coating is formed at this moment, the porosity of which even at this time represents a measure for the finished, dry coating. Thus it is advantageously possible with the use of the innovative process to measure the current flow as a test of porosity immediately after the electrocoating stage, prior to rinsing and drying.

To separate electrically the test voltage from the direct current applied to invoke electrophoresis it is possible to insulate at least one pole of the test circuit electrically from the anode or cathode of the electrocoating system.

The pole formed through direct contact with the strip or profile material or the hollow body can preferably be insulated from the corresponding contact forming the anode or cathode in the electrocoating system.

In this case one pole of the test voltage is applied to the paint in the electrocoating system and is not insulated electrically from the corresponding pole of the direct current required for electrophoresis.

Accordingly, the objects taking the form of hollow bodies can be arranged for electrocoating and for testing the porosity with their openings downward on grids or grates which are electrically conductive but electrically insulated one from the other, while the stream or curtain of liquid for electrocoating and for testing the porosity are in each case directed from beneath through the open spaces between the rods of the grids or grates in the sequentially, mutually electrically insulated sections of the grids or grates.

In accordance with a further development of this process, the objects taking the form of hollow bodies can be arranged for electrocoating with the openings downward on grids or grates which are electrically conductive while the streams or curtain of liquid are in each case directed from beneath through the open spaces between the rods of the grids or grates, the hollow bodies being lifted off the grids or grates for testing the porosity, joined with one pole of the applied test voltage and drenched from below by the stream or curtain of liquid, attached to the other pole of the applied test voltage. In this case it is not necessary to provide for sequential, mutually insulated sections in the grids or grates.

Lifting the hollow bodies off the grids or grates can preferably be done by using magnets to lift ferromagnetic hollow bodies.

The strip or profile material and the objects can be marked and/or automatically rejected if a flow of current exceeding the predeterminable threshold value is registered and can be coated anew, either sectionally or completely, by returning them to the coating system or forwarding them to another, subsequent coating system.

Based on the aforementioned and other objects, the invention further contemplates apparatus for testing the porosity of coated objects, comprising at least one source of measurement voltage, first electrical connection means for connecting the measurement voltage source with the objects, means for generating a continuous stream of liquid and for directing the stream toward a coated surface of the objects, second electrical connection means for connecting the measurement voltage source to the electrolytic liquid, and at least one measurement device for the current flowing from the first electrical connection means through the stream of liquid and the coating to the second electrical connection means to test the porosity of the coating.

The apparatus may feature a marking and/or rejection device actuated by the measurement device.

The innovative apparatus can be designed to test the porosity of an internal coating of ferromagnetic hollow bodies which are electrocoated by being moved slidingly on electrically conductive carrier and guide rails connected to one pole of a source of direct current past nozzles connected to the opposite electrical pole and through which electrolytic liquid is discharged to the interior surface of the hollow bodies. After electrocoating, the hollow bodies pass into an area in which magnetic carrier and guide rails located above the hollow bodies lift the hollow bodies. The magnetic carrier and guide rails and the electrolytic liquid fed to the nozzles are joined by conductive cables with a measurement voltage source. A current measurement device is inserted into one of the cables to test the porosity of the internal coating of the hollow bodies.

Other features and advantages of the present invention will become apparent from the following detailed description of the invention which refers to the accompanying drawings.

BRIEF DESCRIPTION OF THE DRAWING(S)

FIG. 1 is a schematic of apparatus for anodic or cathodic electrocoating of strip or profiled material with subsequent testing in accordance with the present invention of the porosity of the electrocoating; and FIG. 2 is a perspective view of apparatus for anodic or cathodic electrocoating of beverage cans with subsequent testing in accordance with the present invention of the porosity of the inside coating.

DETAILED DESCRIPTION OF THE INVENTION

Figure 1:
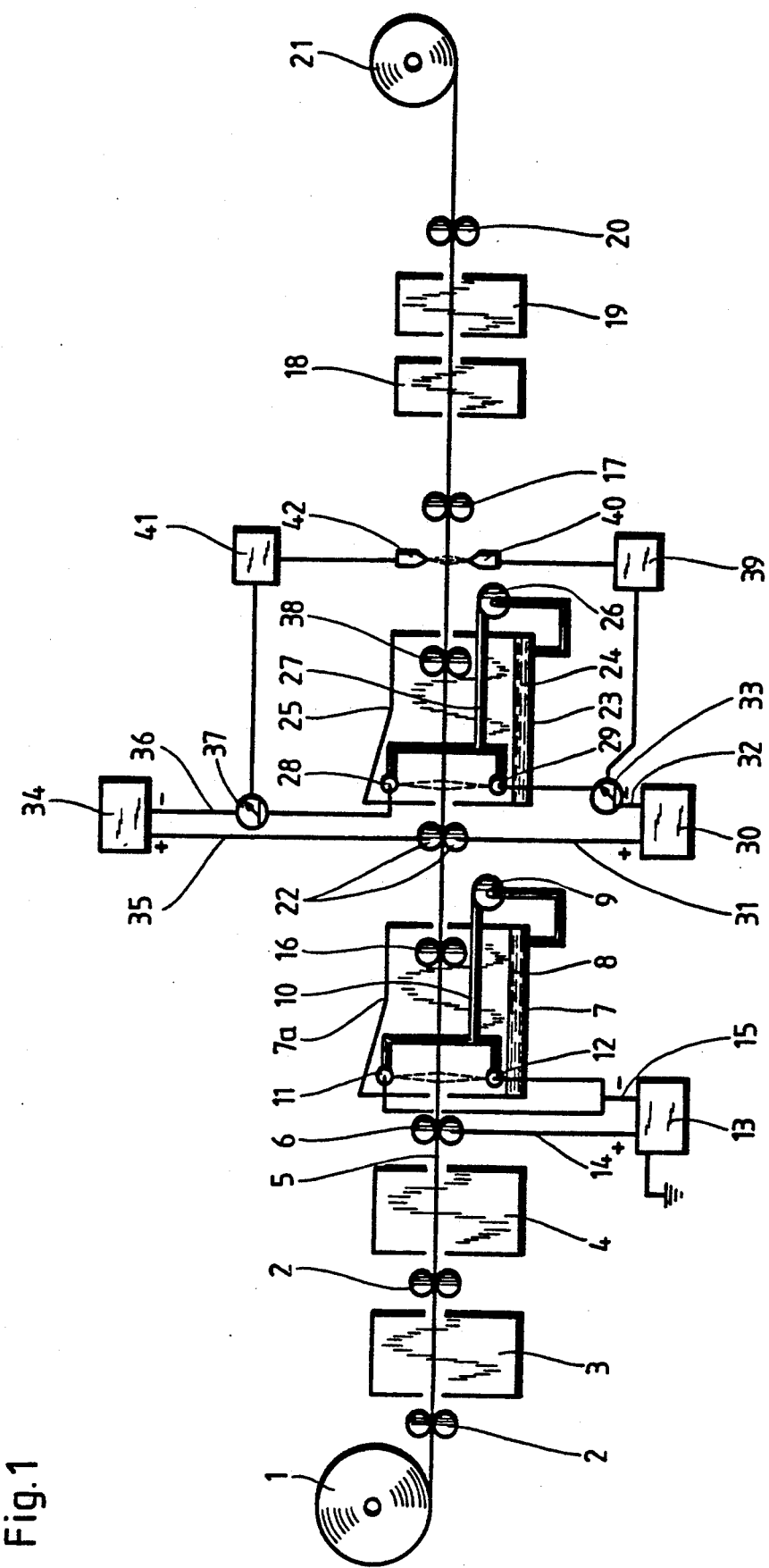

A process and apparatus for anodic or cathodic electrocoating of strip or profiled material are described in U.S. patent application Ser. No. 07/888,048, filed on 22 May 1992, now U.S. Pat. No. 5,264,096, by the same applicant. Reference is made to that patent application, the entire disclosure of which is hereby incorporated by reference, in regard to the details of the process and the apparatus described therein.

The apparatus described in FIG. 1 refers to the coating of strip material 5, but can however be utilized in an analogous fashion for profile materials.

While strip material 5 is unrolled from a coil on a feed reel 1 and passed through the system until it is again rolled up on a take-up reel 21, profile material can be passed through the system straight, whereby this profile material can be introduced into and removed from the system as sectional material or can also be paid out as strip material from a coil located on a feed reel 1, passed through a profiling system not shown and passed through the system as a profile. When electrocoating profiled material, the take-up reel 21 at the end of the system is dispensed with and replaced by a cutting device, so that the profile material may be cut to a desired length.

With reference to the coating of strip material 5, the system is configured as follows: The strip material 5 unrolled from the feed reel 1 is passed through a first pair of conveyor rollers 2, a cleaning unit 3, a further pair of conveyor rollers 2, and a rinsing unit 4 until the horizontal strip material 5 reaches a further pair of rollers 6 which is located immediately in front of a coating system. This pair of rollers 6 is connected by means of a conductor cable 14 with the positive pole of a source of direct current 13 and thus applies to the strip material 5 the positive pole of the direct current source 3 so that the strip material 5 becomes the anode. The positive pole of the direct current supply 13 is grounded, eliminating any need to insulate the entire system. The coating system comprises a drip pan 7 located beneath the strip material 5 to catch electrolytic liquid 8 and a cover hood 7a positioned above the strip material 5. A pump 9 draws electrolytic liquid out of the drip pan 7 and moves it through a pipe 10 to a nozzle 11 located above the strip material 5 and/or to a nozzle 12 located below the strip material. The nozzles 11, 12 cover the entire width of the strip material 5 and apply electrolyte to the surfaces of the strip material 5 in a uniform, continuous stream or curtain of liquid, through which electrical connection is maintained with the nozzles 11, 12 and thus via a conductor cable 15 with the negative pole of the direct current supply 13. The nozzles 11, 12 are electrically insulated from the drip pan 7, the cover hood 7a and the pump 9. As the strip material 5 passes between the nozzles 11, 12 potential is equalized between the strip material 5 functioning as the anode and the nozzles 11, 12 acting as the cathode, this taking place through the stream of electrolytic liquid. Coating particles from the electrolytic liquid thus coagulate on the strip material in its function as the anode, forming a film, whereby the layer thickness can be determined by adjusting the conveyance speed of the strip material, the cross section of the stream, the velocity of the stream, the DC voltage generated by the direct current source 13 and/or the composition of the electrolyte so that a predeterminable layer thickness, varying from one surface to the other if desired, can be achieved.

A pair of squeegee rollers 16 is located inside the space defined by the drip pan 7 and the cover hood 7a; they strip off the non-coagulated electrolytic liquid which is carried along on the strip.

Once the strip material 5 has passed out of the area of the drip pan 7 and the cover hood 7a, a pair of slip contacts 22 makes metallic contact with the surfaces of the strip material 5. Then the strip material 5 passes into the area of a drip pan 23 filled with electrolytic fluid 24, which is covered by a cover hood 25. A pump 26 is used to move electrolytic fluid 24 through a pipe 27 and to an upper slot-type nozzle 28 and to a lower slot-type nozzle 29 so that the surfaces of the strip material 5 will be covered with a continuous layer of electrolytic fluid. The positive pole of a source of measurement voltage 30 is joined with a slip contact 22 by means of a conductor cable 31, while the negative pole is connected via a conductor cable 32 and a current measurement instrument 33 to the lower slot-type nozzle 29. The liquid pumped into the lower slot-type nozzle 29 by means of the pump 26 and which is directed in a continuous curtain of liquid against the surface of the strip material 5 forms a continuous electrical contact which can be utilized to measure the porosity of the coating. If a constant measurement voltage of, for instance, 6.3 V is applied by way of the source of measurement voltage 30, a small current flows through the current measurement instrument 33, which is a measure of the porosity of the coating. If the measured current exceeds a predeterminable threshold value, a signal will pass from the current measurement instrument 33 to a control unit 39 which drives spray nozzles 40 which apply a colored marking to the surface area of the strip material where excessive porosity was detected. The strip material 5 can then be repainted in these marked areas.

A suitable source of measurement voltage 34 is provided for the upper surface of the strip material 5, which is connected via a conductor cable 35 with the upper slip contact 22 and via a conductor cable 36 and a current measurement instrument 37 with the upper slot-type nozzle 28. The operational concept is the same and need not be described again in detail in regard to either the control unit 41 or the spray nozzles 42. Used preferably as the electrolytic fluid is the paint previously used or its permeate, derived through ultrafiltration.

Then the strip material 5 is moved by means of conveyor rollers 17 to a rinsing unit 18 and a dryer unit 19 from which point the strip material 5 is drawn off by a further pair of conveyor rollers 20 and wound up on a take-up reel 21 to again form a coil.

If, as previously mentioned, differing electrolytic liquids are used it is possible in a fashion not illustrated to arrange two drip pans 7 with cover hood 7a, the nozzles 11, 12 located therein, squeegee rollers 16 and a pump 9 one after another in sequence so that, for example, in the first coating step the upper surface of the strip material 5 can be coated with an electrolytic liquid, of a certain color or of a certain composition for instance, to a predeterminable layer thickness and then subsequently, in the following coating unit, the other side of the strip material 5 is coated in the desired fashion. This makes it possible to achieve differing colors on the top and bottom surfaces of the strip material and/or to achieve differing coating thicknesses.

In an analogous fashion it is possible in this case to divide the test apparatus for the porosity of the coating on the upper surface and the lower surface of the strip material 5 so that one test apparatus can be located downline from the painting unit for the lower surface and another apparatus downline of the painting unit for the upper surface.

The apparatus shown in FIG. 2 for anodic or cathodic electrocoating of beverage cans is described in detail in German patent application P 40 05 620.1 dated 22 Feb. 1990 by the same applicant. Reference is made to that patent application, the entire disclosure of which is hereby incorporated by reference, for details.

A hollow metallic body and in particular, as illustrated, a beverage can 43, is positioned on the carrier and guide rails 46 with the bottom of the can 44 upward and the open top 45 downward.

These carrier and guide rails 46 are arranged on edge, one adjacent and parallel to another and separated by a certain distance and are held in place by means of spacers 48 and by nuts 49 and threaded rods not illustrated. The carrier and guide rails 46 form a grate for the beverage cans 43. The narrow edges 47 of the carrier and guide rails 46 supporting the beverage cans 43 are sharpened to razor sharpness so that between the edge of the can at the open top 45 and the carrier and guide rails 46 the contact is in the shape of a point for all practical purposes which insures very good electrical contact between the carrier and guide rails 46 and the beverage cans 43. The beverage cans 43, only two of which are illustrated, are slid longitudinally along the carrier and guide rails 46, on the razor-sharp narrow edges whereby any deposited residues of solids are continuously scraped away so that there is always metallic contact between the razor-sharp narrow edges 47 of the carrier and guide rails 46 and the edge of the can.

Located in the intervening space between the carrier and guide rails 46 are nozzle pipes 50 which are in communication with a housing 51 located below the carrier and guide rails 46. The housing 51 and the nozzle tubes 50 may be fabricated from insulating material if the cathodic electrocoating process is used. The housing 51 comprises an upper section 52 featuring a peripheral flange 55 and a lower section 53 featuring a peripheral flange 56, which are bolted to one another by means of bolts, not shown, inserted in holes 57 in the flanges 55, 56.

The housing 51 is in communication with the nozzle pipes 50 and an electrolyte feed line 58. There is further provided an electrolyte return line 59, so that recirculation is possible for the electrolytic fluid which is not discharged from the nozzle pipes 50.

Inside the housing 51 there is located an electrode of large surface area, not illustrated, which is connected electrically with one pole of a source of direct current 69. The carrier and guide rails 46 are connected accordingly with the other pole of this particular source of direct current. To achieve perfect coating of the inside of the beverage cans 43, the electrolytic fluid discharged from the nozzle pipes 50 must pass in a continuous stream right through to the bottom of the can 44 and spread from there to the entire interior surface of the beverage can 43 so that electrophoresis can take place on this interior surface and a continuous coating of the inside of the can is achieved.

The drawing shows only a section of a larger plant, which carries a large number of hollow bodies, arranged upright, one next to the other, which are in contact with each other and which are moved mutually and commonly in the direction indicated by the arrow 60, i.e. on and in the longitudinal direction along the razor-sharp narrow edges 47.

Wires arranged appropriately could also be used instead of the rails 46. The carrier and guide rails 46 are located above a drip pan 54 to catch dripping electrolytic fluid.

The paint fed through the feed line 58 is connected to the negative pole of a source of measurement voltage 65 by means of a conductor cable 67 and a current measurement instrument 68 whereby the positive pole of this source of measurement voltage 65 is connected by way of a conductor cable 66 with magnetic rails 61, 62 arranged parallel one to another and having narrow edges 63 and 64, respectively. The one magnetic rail 61 forms the magnetic north pole while the other magnetic rail 62 forms the magnetic south pole so that a beverage can 43 passing into the area below these magnetic rails 61, 62 will be lifted off the carrier and guide rails 46 and into contact with the narrow edges 63 and 64 so that the raised beverage cans 43 are in contact only with the positive pole of the source of measurement voltage 65.

Since the internal section of the beverage can 43 continues to be doused by a continuous stream of electrolytic liquid passing through the nozzle pipes 50, i.e. doused with paint, it is possible, as previously described in regard to FIG. 1, to carry out a test of the porosity of the inner coating of the beverage can 43 by means of the flow of current which is indicated by the current measurement instrument 68.

The beverage cans 43 need be lifted only a few millimeters from the carrier and guide rails 46 to effect an interruption in the electrical contact with the source of current for the electrophoresis, so that here, too, an exact determination of the porosity is possible. Permanent magnets could be located between the rails 61, 62 to generate the polarity indicated. Electromagnets could just as well be located between the magnetic rails 61, 62, which would offer the advantage that the magnetic attraction could be optionally switched on and off.

Instead of the magnetic rails 61, 62 located above the beverage cans 43 it would also be possible to provide carrier and guide rails as extensions of the carrier and guide rails 46 shown, which would be separated electrically from the carrier and guide rails 46 shown, by an insulating distance corresponding to the diameter of the beverage cans. A nozzle arrangement in the area of the electrically separated carrier and guide rails would provide in the way previously described an electrical contact between the two poles of the measurement voltage source 65 so that in this case, too, the testing of the porosity of the interior coating could be performed quickly and simply.

The example illustrated here refers to electrocoating of beverage cans by means of streams of electrolytic liquids. The innovative process can, however, also be used in submersion-type electrocoating with or without the assistance of a current of liquid formed underneath the surface of the liquid if at least one pole of the measurement voltage is electrically insulated from one pole for the electrocoating and if the measurement voltage is applied immediately after electrocoating but before rinsing and drying, preferably in the submersion coating bath and the flow of current is measured.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A process for testing the porosity of an electrically conductive object having a first coated surface which has been coated by being subject to electrocoating with a water-based enamel, which process comprises:
    making electrical contact with the object to form a first pole for a test voltage;
    applying an uninterrupted stream of an electrolytic liquid composed of the water-based enamel or its permeate derived through ultrafiltration to the first coated surface of the object to form a second pole for the test voltage;
    applying the test voltage to the first and second poles; and
    measuring the current flowing from the first pole through the stream of liquid and the coating to the second pole to test the porosity of the coating.

2. Process according to claim 1, wherein the object is a strip or profile material having a width and the stream of liquid forms a covering layer extending over the entire width of the strip or profile material.

3. Process according to claim 1, wherein the object is moved continuously through the stream of liquid.

4. Process according to claim 1, wherein the object is moved cyclically through the area of the stream or curtain of liquid.

5. Process according to claim 1, wherein the object has a second coated surface, and which further comprises directing a continuous stream of an electrolytic liquid at the second surface to form a third pole for the test voltage, applying the test voltage to the third pole and measuring the flow of electrical current between the first and third poles to test the porosity of the second coating.

6. Process according to claim 5, wherein the stream directed at the second surface is directed simultaneously with the stream directed at the first surface.

7. Process according to claim 5, wherein the steam directed at the second surface is directed sequentially of the stream directed at the second surface.

8. Process according to claim 1, wherein the object is coated by a process which includes electrocoating and rinsing and the current flow measurement used to test the porosity is performed subsequent to electrocoating but before rinsing and drying.

9. Process according to claim 8, wherein the electrocoating is performed with a system including an anode and a cathode and at least one of the first and second poles is insulated electrically from at least one of the anode and cathode of the electrocoating system.

10. Process according to claim 9, wherein the first pole is insulated from at least one of the anode and cathode of the electrocoating system.

11. Process according to claim 10, wherein the object is hollow and has an open end, electrocoating of the object is effected by subjecting the first surface to a stream of an electrolytic liquid, the object is arranged for electrocoating and for testing its porosity with its open end downward on an electrically conductive grid comprised of a plurality of conductive elements insulated electrically and spaced from each other and which are electrically connected to one of the anode and cathode of the electrocoating system, and the streams of liquid for electrocoating and for testing the porosity are in each case directed from below through the spaces between the grid elements.

12. Process according to claim 10, wherein the object is hollow and has an open end, electrocoating of the object is effected by subjecting the first surface to a stream of an electrolytic liquid, and the object is arranged for electrocoating with its open end downward on an electrically grip conductive comprised of a plurality of conductive elements, lifting the hollow object off the grip to test its porosity, electrical contact is made with the object to form the first pole of the applied test voltage while the object is off the grid and that the streams of liquid forming the other pole of the applied test voltage are directed into the hollow object from below and through the spaces between the grid elements.

13. Process according to claim 1, wherein the object is ferromagnetic and is magnetically lifted from the grid.

14. Process according to claim 1, wherein the object is marked in a portion where the flow of current exceeds a predetermined threshold value.

15. Process according to claim 14, wherein the marked object is recoated at least in the portions marked.

16. Apparatus for testing the porosity of objects having coated surfaces which have been coated by being subject to electrocoating with a water-based enamel, which comprises:
- at least one source of measurement voltage having first and second terminals;
- means for generating an uninterrupted stream of electrolytic liquid composed of the water-based enamel or its permeate derived through ultrafiltration for directing said stream against the coated surfaces of the object;
- first means for electrically connecting the first terminal of the source of measurement voltage to the objects;
- second means for electrically connecting the second terminal of the source of measurement voltage to the stream; and
- means for measuring the current flowing from the first electrically connecting means through the stream of liquid and the coating to the second electrically connecting means to test the porosity of the coating.

17. Apparatus according to claim 16, further including a marking device responsive to the measuring means to mark the surfaces of the objects in portions where the flow of current exceeds a predetermined threshold value.

18. Apparatus for electrocoating the interior surfaces of ferromagnetic hollow bodies having open ends and for testing the porosity of the coatings, which comprises:
- a plurality of spaced, electrically conductive carrier and guide rails upon which the bodies are received with their open ends facing downwardly;
- means for directing a stream of electrolytic liquid into the bodies from below the guide rails through the spaces therebetween;
- means for applying an electrocoating voltage to the rails and to the stream to coat the interior surface of each body;
- means located above the carrier and guide rails for magnetically lifting the bodies off of the rails; and
- means for applying a measurement voltage to the bodies and to the stream and for measuring the current flowing through the bodies and the stream to test the porosity of the coating applied to the bodies.

19. Apparatus in accordance with claim 18, wherein the magnetically lifting means comprises a plurality of magnetic rails positioned above the guide and carrier rails.

* * * * *